United States Patent [19]

Handy et al.

[11] Patent Number: 4,662,213

[45] Date of Patent: May 5, 1987

[54] BACK PRESSURED PNEUMATIC PRESSURE CELL

[75] Inventors: Richard L. Handy; Don W. Eichner, both of Ames, Iowa

[73] Assignee: Iowa State University Research Foundation, Inc., Ames, Iowa

[21] Appl. No.: 825,271

[22] Filed: Feb. 3, 1986

[51] Int. Cl.[4] .................... G01N 33/24; G01N 3/00; G01L 7/08

[52] U.S. Cl. ........................................ 73/37; 73/784; 73/701; 73/716

[58] Field of Search ..................... 73/37, 701, 716, 84, 73/784, 73, 432 SD, 717, 718, 719, 720, 721, 722, 706, 299, 865.6

[56] References Cited

U.S. PATENT DOCUMENTS

| | | | |
|---|---|---|---|
| 2,640,351 | 6/1953 | Jourdain | 73/84 |
| 2,957,341 | 10/1960 | Menard | 73/84 |
| 3,503,254 | 3/1970 | Menard | 73/784 |
| 3,610,035 | 10/1971 | Handy | 73/84 X |
| 3,690,148 | 9/1972 | Snowdon | 73/37 |
| 4,090,397 | 5/1978 | Hancock et al. | 73/716 X |
| 4,091,661 | 5/1978 | Handy. | |
| 4,517,842 | 5/1985 | Twomey et al. | 73/701 |
| 4,524,626 | 6/1985 | Pabst et al. | 73/784 |
| 4,543,820 | 10/1985 | Handy et al. | 73/84 |

Primary Examiner—Stewart J. Levy
Assistant Examiner—Tom Noland
Attorney, Agent, or Firm—Zarley, McKee, Thomte, Voorhees & Sease

[57] ABSTRACT

An improved back-pressured pneumatic pressure cell is provided along with a method of using the same. The device includes at least one sensing cell mounted on a blade for insertion into the soil. The cell includes a perforated outer ring and a perforated central disk separated by a threshold. A resilient membrane covers the outer ring and central disk. A first back-pressure is applied through the perforations of the outer ring to the membrane, while a second back-pressure is applied through the perforations of the central disk to the membrane. The second pressure is slightly less than the first pressure. When the first pressure reaches the soil pressure, the seal between the membrane and the threshold is broken, thereby permitting a momentary reverse flow of pressure through the perforations of the central disk until the first and second pressures equalize, as monitored by a differential pressure gauge. A valve regulates the pressure differential between the first and second pressures. The first pressure, and accordingly the soil pressure, is indicated on a main pressure gauge.

19 Claims, 7 Drawing Figures

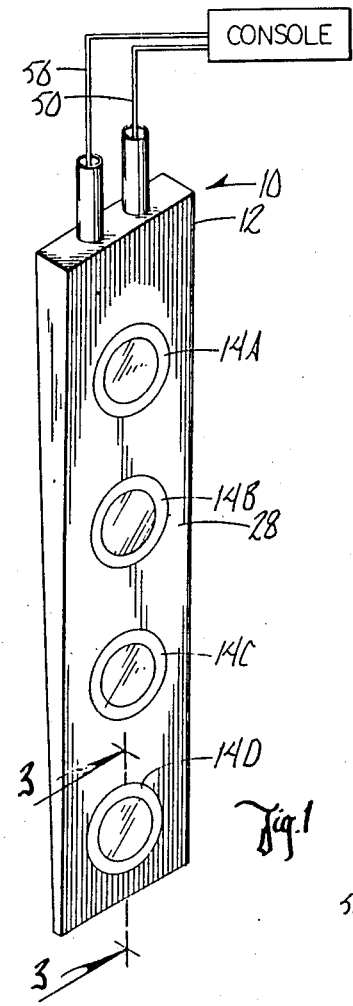
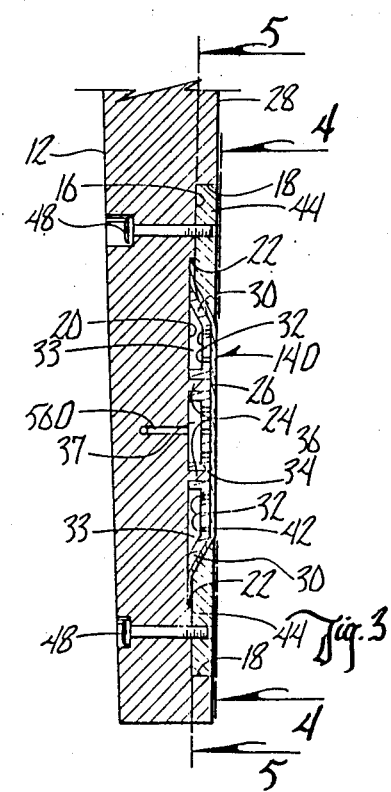
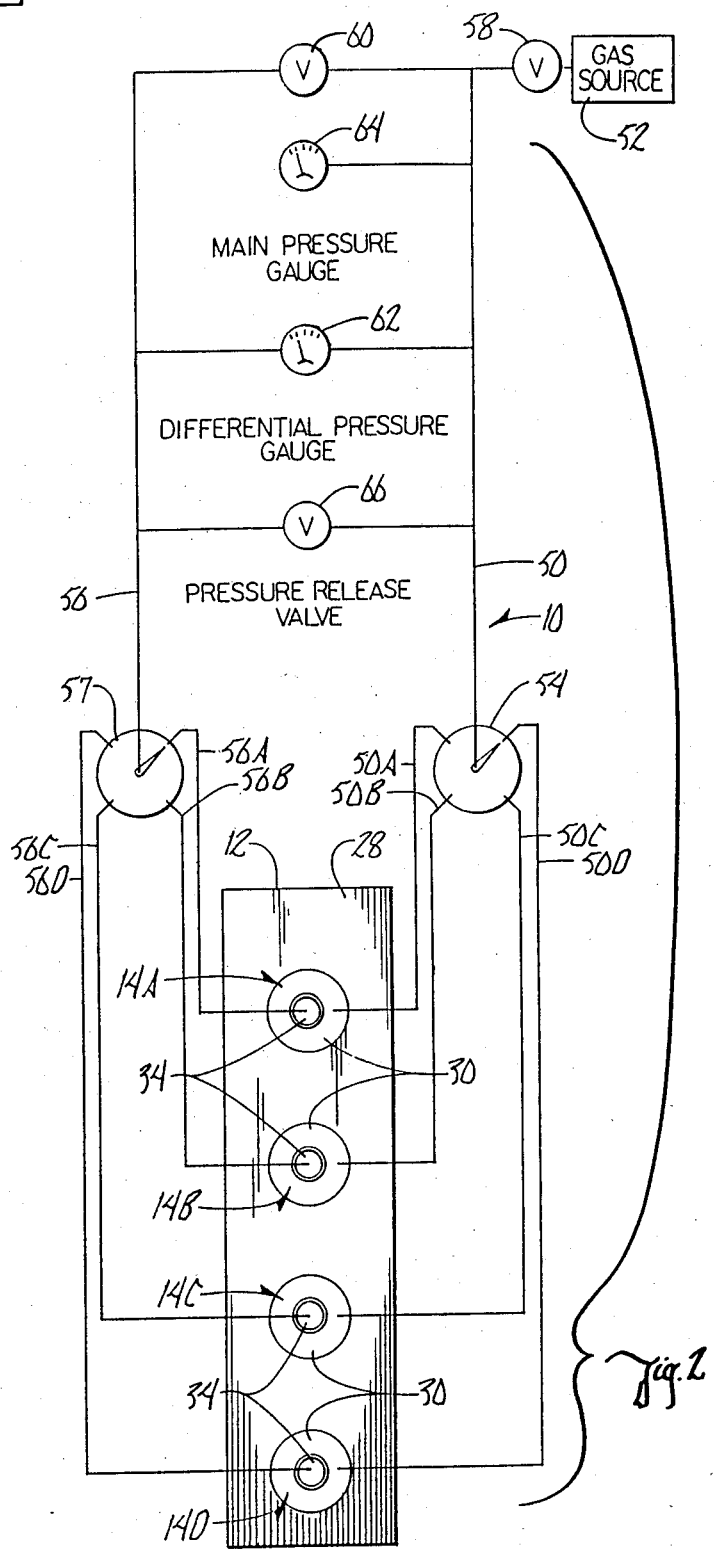

BACK PRESSURED PNEUMATIC PRESSURE CELL

BACKGROUND OF THE INVENTION

Pneumatic cells have been used in the past to measure soil or water pressure. Generally, conventional pneumatic cells include an input tube ending in an orifice, and an output tube ending in an orifice, both orifices being covered by a resilient membrane that acts as a seal. In one application, the pneumatic cell is mounted on a blade for insertion into the soil, and includes a perforated outer ring and a perforated central disk, with the ring and central disk being separated by a threshold. The resilient membrane extends over the outer face of the cell in sealing engagement with the threshold to prevent communication between the perforations of the outer ring and the perforations of the central disk. The use of a conventional pneumatic cell involves the insertion of the blade into the soil such that the membrane engages the soil, or alternately, may involve the contact of fluid pressure to the outer surface of the membrane. A pressure is then applied through the apertures of the outer ring to the back side of the membrane, and is monitored by a main pressure gauge. The pressure is increased until the pressure equals soil pressure wherein the sealing engagement of the membrane with the threshold is broken, thereby allowing the pressure to release across the threshold and flow in a reverse direction through the apertures of the central disk. The detection of such leakage flow by a flowmeter indicates that the soil pressure has been equalized, adjacent the surface of the outer ring, with the reading on the main pressure gauge indicating such soil pressure.

Such conventional pneumatic cells are subject to erroneously high pressure readings. Such error exists because the pressure at the return orifice, or in the case cited above within the apertures of the central disk, remains at atmospheric pressure, thereby leaving the external soil or water pressure unbalanced in the area of the central disk and creating a tendency for the membrane to stick to the threshold.

Therefore, a primary objective of the present invention is the provision of an improved pneumatic pressure cell operating system and a method of using such system which provides accurate soil or water pressure measurements.

A further objective of the present invention is the provision of a back-pressured pneumatic pressure cell and a method of using the same wherein a first pressure is applied to the membrane through the apertures of the outer ring and a second pressure, slightly less than or greater than the first pressure, is applied to the membrane through the apertures of the central disk.

A further objective of the present invention is the provision of a back-pressured pneumatic pressure cell and a method of using the cell wherein the pressure differential between the apertures of the outer ring and the apertures of the central disk is controlled.

SUMMARY OF THE INVENTION

The improved pneumatic cell of the present invention includes a blade adapted to be inserted into the soil and having at least one sensing cell mounted thereon. The cell includes a first perforated outer ring and a second perforated central disk positioned within the outer ring. The outer ring and central disk are separated by a threshold. A resilient membrane covers the cell and is in normally sealing engagement with the threshold when the device is inserted into the soil, thereby preventing communication between the perforations of the outer cell and the perforations of the central disk. The perforations of the outer ring and central disk are in communication with a pressure source such that pressure can be applied through the apertures to the back side of the membrane after the blade has been inserted in the soil. The first pressure applied through the perforations of the outer ring is slightly greater than the second pressure applied through the perforations of the central disk. In operation, such pressure differential is maintained simultaneously as both pressures are increased until the first pressure in the area of the outer ring equals the soil pressure, whereafter the sealing engagement of the membrane with the threshold is broken, thereby momentarily increasing the flow of gas through the apertures of the central disk until the pressures in the perforations of the central disk and perforations of the outer ring equalize. Such equalization of the pressures, as monitored by a differential pressure gauge, indicates that the soil pressure has been reached by the first pressure which is measured on a main pressure gauge.

BRIEF DESCRIPTION OF THE DRAWINGS

FIG. 1 is a perspective view of the pneumatic cell device of the present invention.

FIG. 2 is a schematic showing the operation of the back-pressured pneumatic cell.

FIG. 3 is a partial sectional view taken along lines 3—3 of FIG. 1.

DETAILED DESCRIPTION OF THE DRAWINGS

Figure 4:
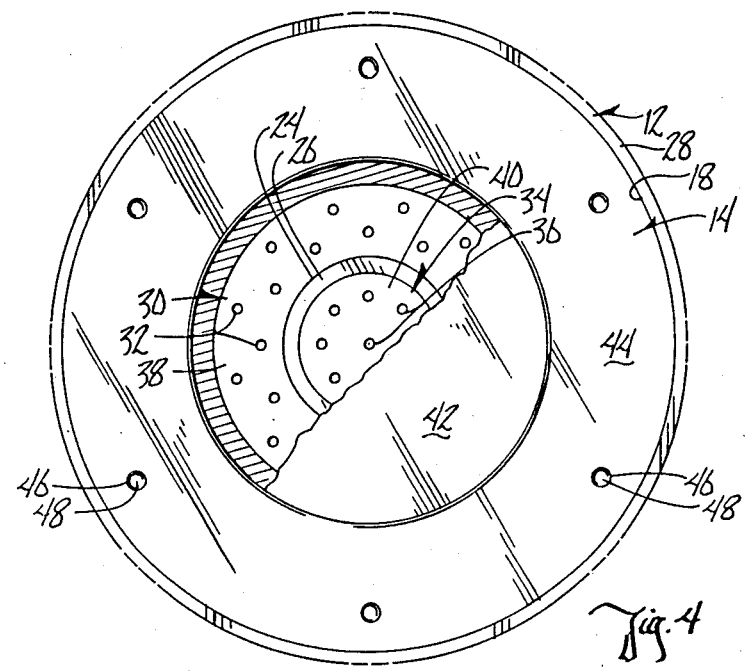
FIG. 4 is an elevational view taken along lines 4—4 of FIG. 3 with a portion of the membrane being removed therefrom.
Figure 5:
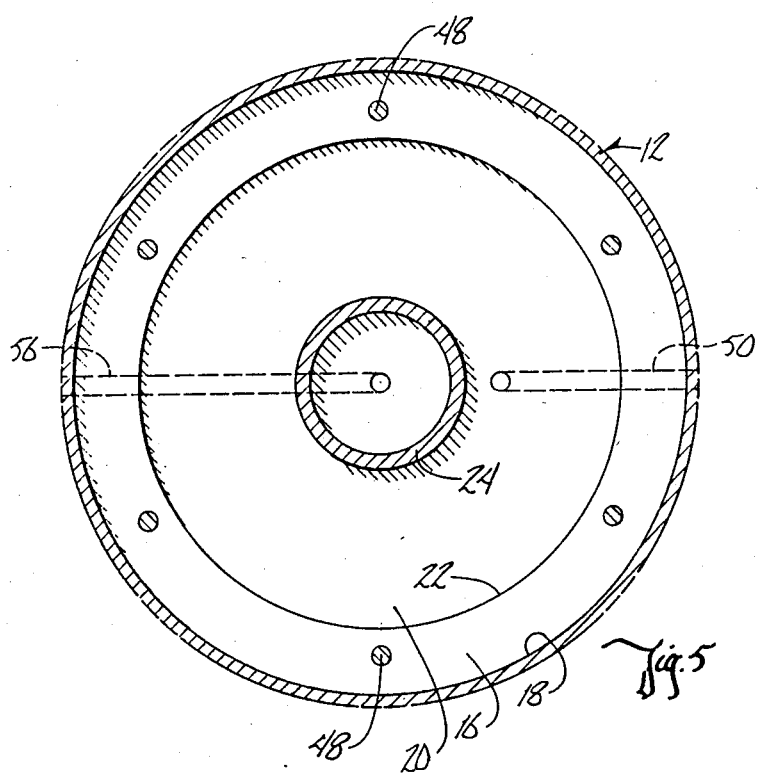
FIG. 5 is a sectional view taken along lines 5—5 of FIG. 3.
Figure 6:
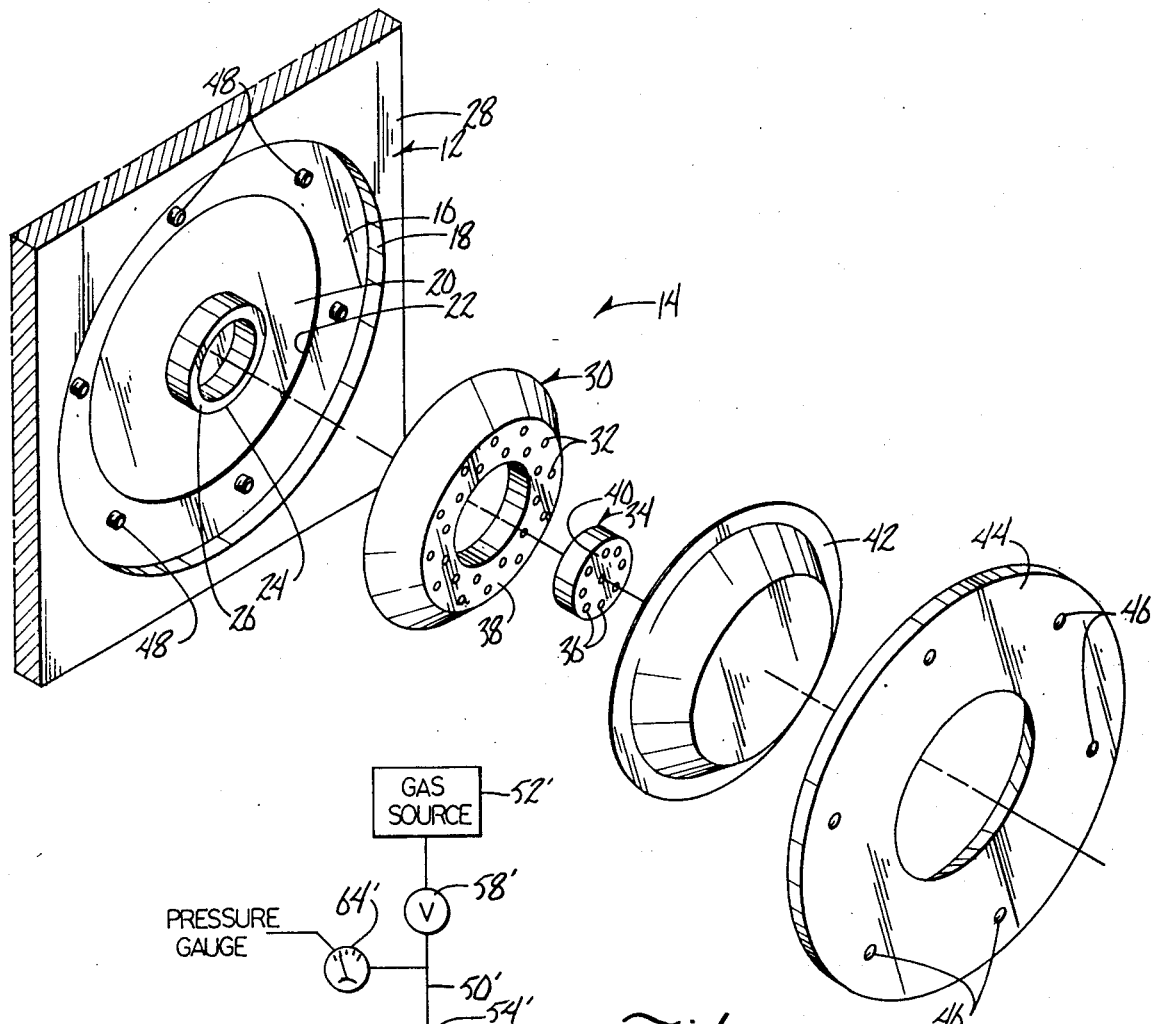
FIG. 6 is an exploded perspective view of the back-pressured pneumatic cell of the present invention.

The back-pressured pneumatic pressure cell of the present invention is generally designated by the reference numeral 10 in the drawings. Device 10 includes a blade 12 adapted to be inserted into the soil and having at least one sensing cell 14 mounted thereon with the surface of the cell being flush with the surface of the blade.

Blade 12 includes a first ring-shaped recessed area 16 having an outer shoulder 18, and a second recessed area 20 within first recessed area 16 and having a perimeter shoulder 22. An axially positioned, ring-shaped threshold 24 extends outwardly from second recessed area 20. The outer surface 26 of threshold 24 is substantially planar with the front surface 28 of blade 12.

Sensing cell 14 includes an outer ring 30 having a plurality of apertures 32 extending therethrough and a central disk 34 having a plurality of apertures 36 extending therethrough. Both ring 30 and disk 34 have recessed areas, 33 and 37, respectively, on their back sides, as best seen in FIG. 3. Ring 30 is adapted to fit around threshold 24 and within second recessed area 20 while central disk 34 is adapted to fit within threshold 24. The outer surface 38 of ring 30 and the outer surface 40 of disk 34 are flush with outer surface 26 of threshold 24 when sensing cell 14 is mounted on blade 12. A resilient membrane 42 fits in covering relation over outer ring 30 and central disk 34. A ring-shaped hold-down plate 44 having a plurality of threaded holes 46 therein is mounted over outer ring 30, central disk 34, and membrane 42 and secured within recessed area 16 of blade 12 by screws 48 or the like. In the alternative, hold-down plate 44 can snap fit into first recessed area 16 of blade 12 to hold outer ring 30, central disk 34 and membrane 42 in place thereon.

The above described structure of blade 12 and sensing cell 14 is conventional and not a part of the present invention.

The present invention improves the operation of the pneumatic pressure cell described above. More particularly, a first pressure line 50 provides communication between a pressure or gas source 52 and the apertures of outer ring 30. When more than one sensing cell is mounted on blade 12, such as cells 14A-D shown in FIG. 2, pressure line 50 can be divided into a plurality of sections 50A-D with a selector valve 54 operatively positioned therein for directing pressure to one of cells 14A-D. A second pressure line 56 provides communication between pressure or gas source 52 and the apertures of central disk 34. Similarly to first pressure line 50, second pressure line 56 can be subdivided into sections 56A-D when a plurality of cells 14A-D are mounted on blade 12, with a second selector valve 57 being disposed in line 56 for directing pressure to one of the cells. While the drawings show both pressure lines 50 and 56 connected to the same pressure source 52, it is understood that each line could be connected to separate sources of pressure. A first valve 58 controls the flow of a first pressure from pressure source 52 to first pressure line 50. A second valve 60 controls the flow of a second pressure from pressure source 52 to second pressure line 56. Valve 60 is adjusted such that the second pressure within line 56, and accordingly the apertures of central disk 34, is slightly less than the first pressure within line 50 and accordingly the apertures of outer ring 30. A differential pressure gauge 62 monitors the pressure differential between lines 50 and 56, with such pressure differential preferably being less than 10 psi. A main pressure gauge 64 monitors the pressure within line 50. A release valve 66 vents the pressure within lines 50 and 56 to the atmosphere. Recessed portion 33 of ring 30 distributes the first pressure equally to all the apertures 32 of the outer ring, while recessed portion 37 of disk 34 distributes the second pressure equally to all the apertures 36 the the central disk.

In operation, blade 12 is inserted into the soil such that membrane 42 is in direct contact with the soil. The soil pressure on membrane 42 effectively seals the membrane against threshold 24 to normally prevent communication between the apertures of outer ring 30 and the apertures of central disk 34. Valve 58 is then opened such that the first pressure is applied through apertures 32 of outer ring 30 to the back side of membrane 42, while valve 60 is opened to apply the second pressure through apertures 36 of central disk 34 to the back side of membrane 42. valve 60 is adjustable to regulate and maintain the pressure differential between the first pressure in the outer ring area and the second pressure in the central disk area, with the second pressure being slightly less than the first pressure. Such pressure differential is monitored by gauge 62, while gauge 64 monitors the first pressure.

The first and second pressures are simultaneously increased by further opening valve 58 until the first pressure equals the soil pressure. It is not necessary to further adjust valve 60 to maintain a constant differential between the first and second pressures. When the soil pressure and first pressure equalize, membrane 42 pushes outwardly against the soil sufficiently so as to break the seal between the membrane and threshold 24, such that the pressure in line 56 momentarily reverses until the first and second pressures are equalized, as indicated by the reading on the differential pressure gauge 62 dropping to zero. The first pressure indicated on pressure gauge 64 at the time the first and second pressures equalize is the equivalent of the soil pressure. After such soil pressure is determined, release valve 66 is opened to vent the pressures within lines 50 and 56 to the atmosphere to prevent damage to the device.

By providing the back-pressure to the central disk area of cell 14, the pressure of the soil is substantially balanced across the entire surface of cell 14, thereby eliminating any tendency for membrane 42 to stick to threshold 24 such that accurate soil pressure readings are obtained by device 10.

Figure 7:
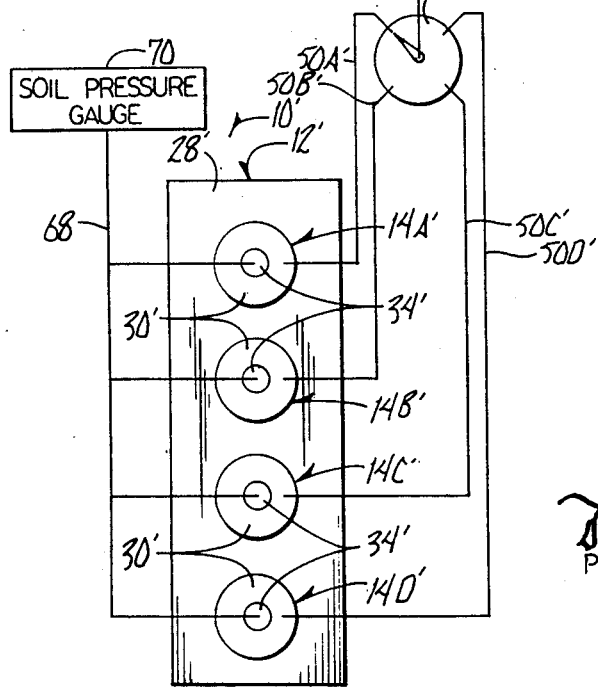
FIG. 7 is a schematic of a prior art pneumatic cell.

For purposes of comparison, FIG. 7 shows a schematic of a prior art pneumatic pressure cell. Similar components are labeled with identical numbers to that of the device of the present invention described above, with the addition of a "'". The primary difference between device 10 of the present invention and the prior art pneumatic pressure cell is the application of a back pressure through line 56 and apertures 36 of central disk 34 to membrane 42 in the present invention. As seen in FIG. 7, pressure from gas source 52' is applied to the membrane only through pressure line 50' and the apertures of outer ring 30'. Only atmospheric pressure is present in the apertures of central disk 34', thus creating a tendency for the membrane to stick to the threshold and produce erroneously high seal pressure readings. When the pressure in the outer ring area of the prior art device reaches the soil pressure, the seal between the membrane and the threshhold is supposed to break such that the pressure leaks across the threshhold and momentarily flows in a reverse direction through the apertures of central disk 34' and through a pressure line 68 to a gauge 70, wherein the pressure on gauge 70 represents the soil pressure. However, the large pressure differential between the apertures of central disk 34' and the apertures of the outer ring 30' creates a tendency for the membrane to stick to the threshhold, thereby requiring greater pressure in the outer ring area to break the membrane seal, thus producing erroneously high soil pressure measurements.

The application of back-pressure through the central disk at a level slightly less than the back-pressure applied through the outer ring, as in the present invention, overcomes the inaccurate measurements of the prior art devices. Thus, the back-pressured pneumatic cell device 10 of the present invention improves upon the prior art pneumatic cells to produce more accurate soil pressure determinations. Also, device 10 of the present invention accomplishes at least all of the stated objectives.

What is claimed is:

1. A method of measuring soil or fluid pressure using a pneumatic cell and having first and second perforated portions separated by a threshold and a resilient membrane secured over said first and second portions, said method comprising:

inserting said cell into the soil or fluid such that said membrane engages the soil or fluid and sealingly engages said threshold to prevent communication between the perforations of said first portion and the perforations of said second portion;

applying a first pressure through the perforations of said first portion of said cell to said membrane, applying a second pressure through the perforations of said second portion of said cell to said membrane, said second pressure being less than said first pressure;

increasing said first and second pressures while maintaining a pressure differential therebetween until said membrane moves out of sealing engagement with said threshold so as to provide communication between the perforations of said first portion and the perforations of said second portion whereby said first and second pressures equalize, said first pressure being equal to the soil or fluid pressure when said first and second pressures equalize.

2. The method of claim 1 further comprising monitoring said first pressure and the pressure differential between said first and second pressures.

3. The method of claim 1 further comprising venting said first and second pressures after equalization thereof.

4. The method of claim 1 further comprising regulating said pressure differential during said increase of said first and second pressures.

5. The method of claim 1 wherein said pressure differential between said first and second pressures remains constant until said membrane moves out of sealing engagement with said threshold.

6. The method of claim 1 wherein said pressure differential is less than 10 psi.

7. The method of claim 1 wherein said second pressure is greater than atmospheric pressure.

8. A back-pressured pneumatic pressure cell device for measuring soil or fluid pressure, comprising:

a blade member adapted to be inserted into the soil or fluid and having opposite front and rear surfaces;

at least one sensing cell having opposite front and rear surfaces and being mounted in said blade such that said front surface of said cell is substantially flush with said front surface of said blade;

said sensing cell including first and second portions each having a plurality of apertures extending therethrough and being separated by a threshold, and a resilient membrane on said front surface of said cell in normally sealing engagement with said threshold when said blade is inserted in the soil or fluid so as to normally prevent communication between said apertures of said first portion and said apertures of said second portion;

first pressure means for applying a first pressure through said apertures of said first portion of said cell to said membrane;

second pressure means for applying a second pressure through said apertures of said second portion of said cell to said membrane;

said first pressure being greater than said second pressure;

said membrane being adapted to move out of sealing engagment with said threshold when said first pressure equals said soil or fluid pressure thereby providing communication between the apertures of said first and second portions of said cell such that said first and second fluid pressures equalize.

9. The device of claim 8 further comprising first gauge means for monitoring said first pressure.

10. The device of claim 9 further comprising second gauge means for monitoring the pressure differential between said first and second pressures.

11. The device of claim 8 wherein said first pressure means includes a first passage in said blade having a first end in communication with said apertures of said first portion of said cell and a second end in communication with a pressure source and said second pressure means includes a second passage in said blade having a first end in communication with said apertures of said second portion of said cell and a second end in communication with a pressure source.

12. The device of claim 11 wherein said first and second pressure means are in communication with a single pressure source and with one another.

13. The device of claim 12 further comprising a first valve disposed between said first and second pressure means for regulating the pressure differential therebetween.

14. The device of claim 8 further comprising pressure release means releasing said first and second pressures from said first and second portions of said cell.

15. The device of claim 8 wherein said first portion of said cell is ring-shaped and said seond portion of said cell is disk-shaped and positioned within said first portion.

16. The device of claim 8 further comprising a plurality of said sensing cells mounted on said blade, and switch means for directing said first and second pressures to said first and second portions, respectively, of one of said cells.

17. An improvement in a pneumatic cell device for measuring soil or fluid pressure, said device including a blade, a sensing cell mounted on said blade and having a first perforated portion and a second perforated portion, said first and second portions being separated by a threshold extending therebetween, a resilient membrane covering said first and second portions and normally in sealing engagement with said threshold when said blade is inserted into the soil or fluid thereby normally preventing communication between the perforations of said first portion and the perforations of said second portion, and first pressure means for applying a first pressure through the perforations of said first portion of said cell to said membrane; said improvement comprising:

second pressure means for applying a second pressure through the perforations of said second portion of said cell to said membrane, said second pressure being less than said first pressure, thereby substantially balancing the pressure exerted by said first and second portions of said cell on the soil or fluid such that said membrane moves out of sealing engagement with said threshold without sticking thereto to provide communication between the apertures of said first and second portions when said first pressure equals the pressure of the soil or fluid.

18. The improvement of claim 17 further comprising valve means for regulating the pressure differential between said first and second portions of said cell.

19. The improvement of claim 18 further comprising gauge means for monitoring the pressure differential between said first and second portions of said cell.

* * * * *